US012262753B2

(12) United States Patent
Li et al.

(10) Patent No.: US 12,262,753 B2
(45) Date of Patent: Apr. 1, 2025

(54) ELECTRONIC ATOMIZATION APPARATUS

(71) Applicant: LUXSHARE PRECISION INDUSTRY CO., LTD., Shenzhen (CN)

(72) Inventors: Huabing Li, Shenzhen (CN); Yu Huang, Shenzhen (CN)

(73) Assignee: LUXSHARE PRECISION INDUSTRY CO., LTD., Shenzhen (CN)

( * ) Notice: Subject to any disclaimer, the term of this patent is extended or adjusted under 35 U.S.C. 154(b) by 502 days.

(21) Appl. No.: 17/572,136

(22) Filed: Jan. 10, 2022

(65) Prior Publication Data
US 2022/0361588 A1    Nov. 17, 2022

(30) Foreign Application Priority Data

May 12, 2021    (CN) .......................... 202110518876.5

(51) Int. Cl.
     *A24F 40/51*      (2020.01)
     *A24F 40/10*      (2020.01)
     (Continued)

(52) U.S. Cl.
CPC .............. *A24F 40/60* (2020.01); *A24F 40/30* (2020.01); *A24F 40/46* (2020.01); *A24F 40/53* (2020.01); *A24F 40/65* (2020.01)

(58) Field of Classification Search
None
See application file for complete search history.

(56) References Cited

U.S. PATENT DOCUMENTS 5,269,327 A * 12/1993 Counts .................... A24F 40/30
                                                                   131/194
9,498,002 B1 * 11/2016 Soreide ................... A24F 40/30
(Continued)

FOREIGN PATENT DOCUMENTS

| CN | 203952429 U | 11/2014 |
| CN | 105125222 A | 12/2015 |

(Continued)

OTHER PUBLICATIONS

United Kingdom Search and Examination Report for United Kingdom Application No. 2117797.7, dated Sep. 23, 2022.
(Continued)

*Primary Examiner* — Philip Y Louie
*Assistant Examiner* — Eric M Fierce
(74) *Attorney, Agent, or Firm* — Birch, Stewart, Kolasch & Birch, LLP

(57) ABSTRACT

Provided is an electronic atomization apparatus in the technical field of atomization. The electronic atomization apparatus includes a main unit and an atomizer. The main unit includes a housing component, a control assembly, and a battery assembly. The control assembly and the battery assembly are disposed inside the housing component. The control assembly is electrically connected to the battery assembly. The atomizer includes an atomization housing and a heating circuit disposed inside the atomization housing. One end of the atomization housing is connected to one end of the housing component. The atomization housing is provided with at least two atomization compartments that are independent of each other. The heating circuit is electrically connected to the control assembly. Another end of the atomization housing is provided with a gas outlet. The gas outlet may selectively communicate with one of the at least two atomization compartments.

9 Claims, 4 Drawing Sheets

(51) Int. Cl.
*A24F 40/30* (2020.01)
*A24F 40/40* (2020.01)
*A24F 40/42* (2020.01)
*A24F 40/46* (2020.01)
*A24F 40/53* (2020.01)
*A24F 40/60* (2020.01)
*A24F 40/65* (2020.01)
*A24F 40/90* (2020.01)

(56) References Cited

U.S. PATENT DOCUMENTS

| | | |
|---|---|---|
| 2003/0154991 A1 | 8/2003 | Fournier et al. |
| 2013/0300350 A1 | 11/2013 | Xiang |
| 2016/0106936 A1 | 4/2016 | Kimmel |
| 2017/0027232 A1* | 2/2017 | Scheck ................ A24F 40/51 |
| 2017/0251721 A1 | 9/2017 | Rostami et al. |
| 2020/0029618 A1 | 1/2020 | Fraser et al. |
| 2020/0060340 A1* | 2/2020 | Hejazi ................ A24F 40/42 |
| 2020/0128877 A1* | 4/2020 | Sur ................ A24F 40/49 |
| 2020/0205478 A1 | 7/2020 | Dick et al. |
| 2021/0368865 A1* | 12/2021 | Ki ................ H05B 1/0227 |
| 2023/0051230 A1* | 2/2023 | Batista ................ A24F 40/30 |
| 2023/0284683 A1* | 9/2023 | Hazani ................ A24F 40/465 |

FOREIGN PATENT DOCUMENTS

| | | |
|---|---|---|
| CN | 109007975 A | 12/2018 |
| CN | 110419780 A | 11/2019 |
| CN | 110754694 A | 2/2020 |
| CN | 111213914 A | 6/2020 |
| CN | 215684809 U | 2/2022 |
| EP | 3 554 190 A1 | 10/2019 |
| WO | WO 2021/071305 A2 | 4/2021 |

OTHER PUBLICATIONS

Chinese Office Action and Search Report for Chinese Application No. 202110518876.5, dated Sep. 28, 2024, with English translation.

* cited by examiner

ELECTRONIC ATOMIZATION APPARATUS

CROSS-REFERENCE TO RELATED APPLICATION(S)

This application claims priority to Chinese Patent Application No. 202110518876.5, filed May 12, 2021, the disclosure of which is incorporated herein by reference in its entirety.

TECHNICAL FIELD

The present disclosure relates to the technical field of atomization, in particular, an electronic atomization apparatus.

BACKGROUND

Currently, an electronic atomization apparatus commonly includes a main unit and an atomizer. The main unit is configured to provide electricity for the atomizer. The atomizer is configured to heat a liquid or solid substance to be atomized into a mist. The atomizer includes a heating structure and an atomization compartment surrounding the heating structure. The substance to be atomized is placed inside the atomization compartment so that the heating structure can heat the substance inside the atomization compartment and generate a mist. When the type of the substance to be atomized inside the atomization compartment needs to be changed, the atomizer is usually replaced with a new one due to the complex structure and difficult disassembly of the atomizer. Then a new substance to be atomized is placed inside the new atomizer. Since the atomizer needs to be replaced each time the thoroughfare of the electronic atomization apparatus changes, the atomizer has become consumable. In this case, the cost of the electronic atomization apparatus is relatively high and multiple uses of one atomizer cannot be achieved.

SUMMARY

An object of the present disclosure is to provide an electronic atomization apparatus so that different types of substances to be atomized are accommodated separately in different atomization compartments with no need for replacing an atomizer. In this case, multiple uses of the atomizer are achieved and the cost of the electronic atomization apparatus is relatively low.

To achieve this object, the present disclosure provides solutions below.

The electronic atomization apparatus includes a main unit and an atomizer.

The main unit includes a housing component, a control assembly, and a battery assembly. The control assembly and the battery assembly are disposed inside the housing component. The control assembly is electrically connected to the battery assembly.

The atomizer includes an atomization housing and a heating circuit disposed inside the atomization housing. One end of the atomization housing is connected to one end of the housing component. The atomization housing is provided with at least two atomization compartments that are independent of each other. The heating circuit is electrically connected to the control assembly. Another end of the atomization housing is provided with a gas outlet. The gas outlet is selectively communicated with one of the at least two atomization compartments.

In an embodiment, one end of the atomization housing is detachably connected to one end of the housing component.

In an embodiment, the electronic atomization apparatus further includes a nozzle. The nozzle is connected to another end of the atomization housing and communicated with the gas outlet.

In an embodiment, the control assembly includes a control module and a wireless communication module electrically connected to the control module. The heating circuit is electrically connected to the control module. The wireless communication module is able to receive a wireless control signal. The control module is able to control the heating circuit to turn on or off according to the wireless control signal. The wireless control signal includes the information of turning on or the information of turning off.

In an embodiment, the control assembly further includes a biomonitoring module. The biomonitoring module is electrically connected to the control module and is configured to monitor the user-biometric information. The user-biometric information includes the body temperature or the heart rate.

In an embodiment, at least two heating circuits are provided. The at least two heating circuits are electrically connected to the control module separately and are in one-to-one correspondence with the at least two atomization compartments. Each heating circuit is configured to heat a corresponding atomization compartment.

In an embodiment, the battery assembly includes a graphene battery.

In an embodiment, the electronic atomization apparatus further includes a wireless charging assembly electrically connected to the battery assembly.

In an embodiment, the housing component includes a housing and a separator secured inside the housing. One end of the atomization housing is connected to one end of the housing. The separator separates the housing into a battery cavity and an electronic cavity. The battery assembly is secured inside the battery cavity. The control assembly is secured inside the electronic cavity. The wireless charging assembly is secured on the housing and disposed at the end of the battery assembly.

In an embodiment, the electronic atomization apparatus further includes a touch display panel disposed on the housing. The touch display panel is electrically connected to the control assembly.

The present disclosure at least has beneficial effects below.

As for the electronic atomization apparatus provided in this embodiment, the atomizer is provided with at least two atomization compartments. With this arrangement, the at least two atomization compartments may include a healthcare chamber for accommodating a healthcare product, a medical chamber for accommodating a medicine, and a tar chamber for accommodating a tobacco tar. When a user needs to use the electronic atomization apparatus for healthcare, the healthcare chamber may be heated through a heating circuit controlled by the control assembly. Moreover, the gas outlet is made to communicate with the healthcare chamber. In this manner, the healthcare chamber generates a mist exiting from the gas outlet. When the user needs to use the electronic atomization apparatus for medical treatment, the medical chamber may be heated through a heating circuit controlled by the control assembly. Moreover, the gas outlet is made to communicate with the medical chamber. In this manner, the medical chamber generates a mist exiting from the gas outlet. Accordingly, the electronic atomization apparatus can perform various functions with no need for replacing the atomizer. In this case, multiple uses of the atomizer are achieved and the cost of the electronic atomization apparatus is relatively low.

Figure 1:
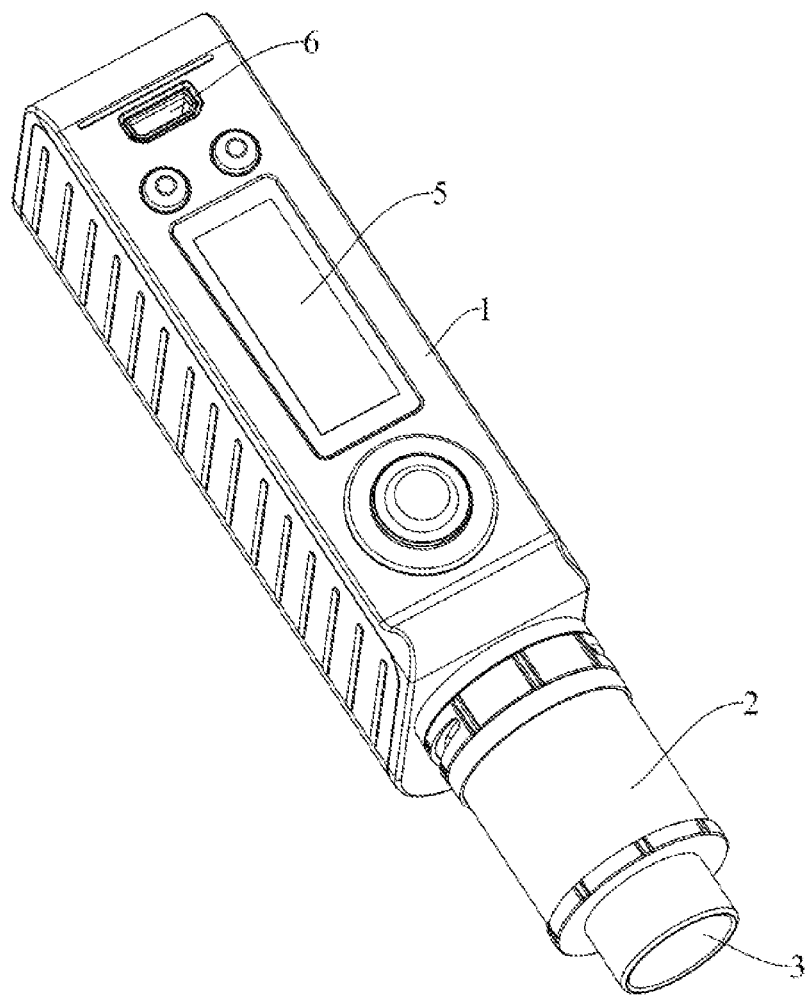
FIG. 1 is a view illustrating the structure of an electronic atomization apparatus according to embodiments of the present disclosure.

REFERENCE LIST 1 main unit
11 housing component
111 first sub-housing
112 separator
113 second sub-housing
12 control assembly
121 control module
122 wireless communication module
123 biomonitoring module
124 music module
13 battery assembly
14 circuit board
2 atomizer
21 atomization compartment
22 atomization housing
3 nozzle
4 wireless charging assembly
5 touch display panel
6 USB-C data charging connector
7 APP

DETAILED DESCRIPTION

To make solved problems, adopted solutions and achieved effects of the present disclosure clearer, solutions of the present disclosure are further described hereinafter in conjunction with drawings and embodiments. It is to be understood that embodiments described hereinafter are intended to explain the present disclosure and not to limit the present disclosure. For ease of description, only a part, not all, related to the present disclosure is illustrated in the drawings.

In the description of the present disclosure, it should be understood that the orientational or positional relationships indicated by terms "center", "above", "below", "left", "right", "vertical", "horizontal", "inside", "outside" and the like are based on the orientational or positional relationships illustrated in the drawings, which are for the mere purpose of facilitating and simplifying the description of the present disclosure, and these relationships do not indicate or imply that the apparatus or component referred to has a specific orientation and is constructed and operated in a specific orientation, and thus it is not to be construed as limiting the present disclosure. Moreover, terms like "first" and "second" are merely for describing the object and are not to be construed as indicating or implying relative importance.

In the description of the present disclosure, it should be noted that unless otherwise expressly specified and limited, terms like "mounted", "connected to each other", "connected" are to be construed in a broad sense, for example, as permanently connected or detachably connected; mechanically connected or electrically connected; directly connected or indirectly connected via an intermediate medium; or internally connected of two elements. For those of ordinary skill in the art, specific meanings of the preceding terms in the present disclosure may be understood based on specific situations.

This embodiment provides an electronic atomization apparatus. An atomizer 2 is provided with a plurality of atomization compartments 21 so that different types of substances to be atomized are accommodated separately in different atomization compartments 21 without replacing the atomizer 2. In this case, multiple uses of the atomizer 2 are achieved and the cost of the electronic atomization apparatus is relatively low.

As shown in FIGS. 1 to 7, the electronic atomization apparatus includes a main unit 1, an atomizer 2, and a nozzle 3. The main unit 1 includes a housing component 11, a control assembly 12, and a battery assembly 13. The control assembly 12 and the battery assembly 13 are disposed inside the housing component 11. The control assembly 12 is electrically connected to the battery assembly 13 to enable that the battery assembly 13 provides electricity for the control assembly 12.

The preceding atomizer 2 includes an atomization housing 22 and a heating circuit disposed inside the atomization housing 22. One end of the atomization housing 22 is connected to one end of the housing component 11. The atomization housing is provided with at least two atomization compartments 21 for accommodating the substances to be atomized. The at least two atomization compartments 21 are independent of each other to enable that the substance in one atomization compartment 21 does not enter other atomization compartments 21 due to the vibration of the electronic atomization apparatus. In this case, the purity of the substance to be atomized in each atomization compartment 21 is guaranteed.

The heating circuit is electrically connected to the control assembly 12 so that the control assembly 12 controls the heating circuit to turn on or off. When the control assembly 12 controls the heating circuit to turn on, the heating circuit can heat the substance in one of the atomization compartments 21 to make the substance in the atomization compartment 21 generate a mist. At the same time, substances in other atomization compartments 21 are not heated. In this case, the electronic atomization apparatus can only generate one type of mist at a time, thus prevented from getting the atomizing gases mixed. Another end of the atomization housing 22 is provided with a gas outlet. The gas outlet selectively communicates with one of the at least two atomization compartments. In an embodiment, the gas outlet communicates with an atomization compartment 21 where a mist can be generated. In this case, the mist exits smoothly from the gas outlet.

As for the electronic atomization apparatus provided in this embodiment, the atomizer 2 is provided with at least two atomization compartments 21. With this arrangement, the at least two atomization compartments 21 may include a healthcare chamber for accommodating a healthcare product, a medical chamber for accommodating a medicine, and a tar chamber for accommodating a tobacco tar. When a user needs to use the electronic atomization apparatus for healthcare, the healthcare chamber may be heated through a heating circuit controlled by the control assembly 12. Moreover, the gas outlet is made to communicate with the healthcare chamber. In this manner, the healthcare chamber generates a mist exiting from the gas outlet. When the user needs to use the electronic atomization apparatus for medical treatment, the medical chamber may be heated through a heating circuit controlled by the control assembly 12. Moreover, the gas outlet is made to communicate with the medical chamber. In this manner, the medical chamber generates a mist exiting from the gas outlet. Accordingly, the electronic atomization apparatus can perform various functions with no need for replacing the atomizer 2. In this case, multiple uses of the atomizer 2 are achieved and the cost of the electronic atomization apparatus is relatively low.

Figure 4:
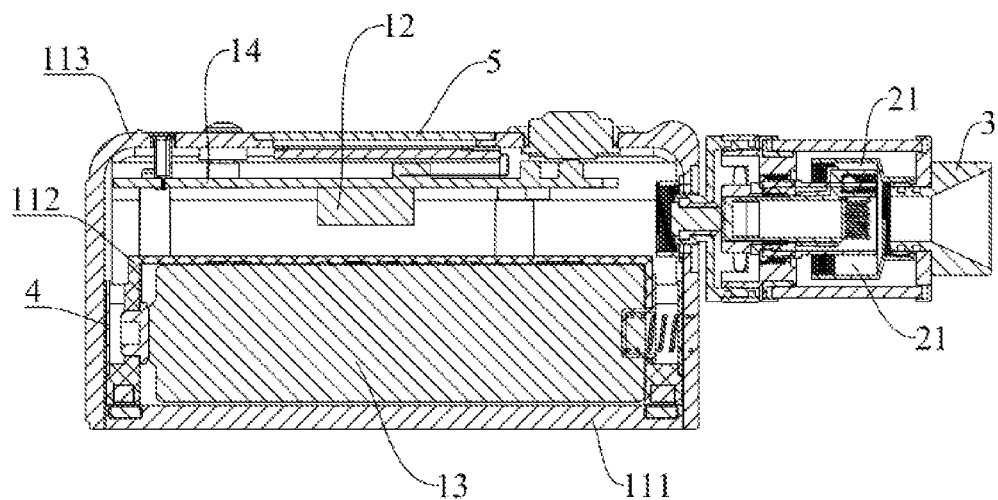
FIG. 4 is a section view taken along A-A of FIG. 3 in the present disclosure.
Figure 5:
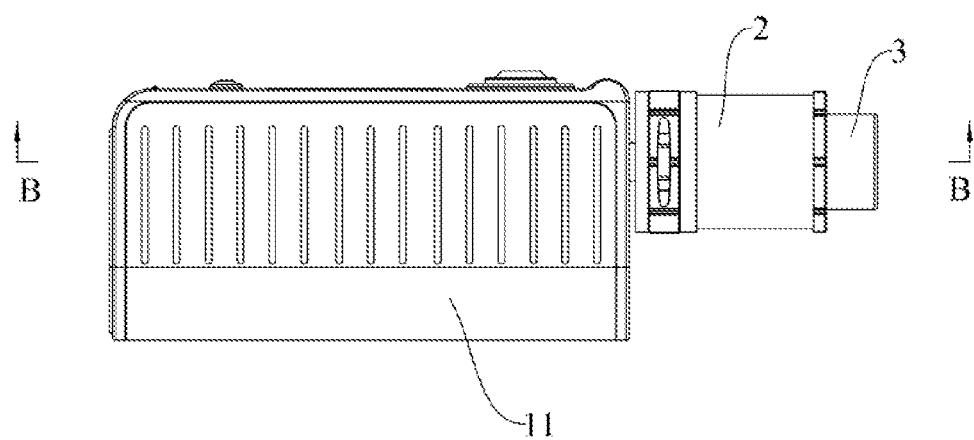
FIG. 5 is a side view of an electronic atomization apparatus according to embodiments of the present disclosure.
Figure 6:
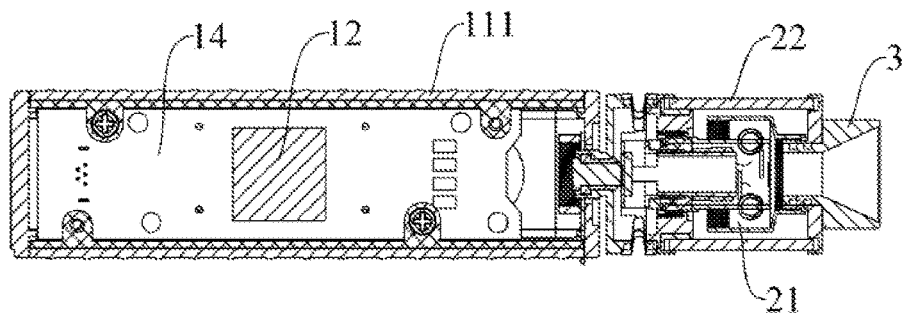
FIG. 6 is a section view taken along B-B of FIG. 5 in the present disclosure.

In an embodiment, one end of the atomization housing 22 is detachably connected to one end of the housing component 11 to facilitate the disassembly and installation of the atomizer 2 and the main unit 1. In this case, the atomizer 2 in this embodiment is replaceable but the replacement frequency is relatively low. In this case, the cost of the electronic atomization apparatus is reduced. Exemplarily, as shown in FIG. 4, the atomizer 2 is engaged with the housing component 11 of the main unit 1 through external threads and internal threads. It is to be understood that the atomizer 2 may be detachably connected to the housing component 11 through other modes including fastening.

In this embodiment, as shown in FIG. 1, the electronic atomization apparatus further includes a nozzle 3. The nozzle 3 is connected to another end of the atomization housing 22 in a replaceable manner and communicates with the gas outlet. In this case, the mist generated in an atomization compartment 21 may enter the nozzle 3 through the gas outlet and thus be inhaled by the user. The replaceable nozzle 3 facilitates the replacement of the nozzle 3 when different types of mists are inhaled and helps avoid being tainted by odor. Exemplarily, as shown in FIG. 4, a channel in the nozzle 3 is trumpet-shaped. The cross-sectional area of the end of the channel facing the atomization housing 22 is smaller than the cross-sectional area of the end of the channel facing away from the atomization housing 22. In this case, the mist in an atomization compartment 21 is diffused in the mouth of the user through the trumpet-shaped channel.

In this embodiment, the nozzle 3 is made of sterile plastics. Moreover, part of the atomization housing 22 for forming the atomization compartments 21 is made of sterile plastics. The sterile plastics have the function of self-sterilization so as to improve the cleanness of the electronic atomization apparatus.

In an embodiment, the heating circuit may heat the substance in one of the atomization compartments 21 in various modes. This embodiment provides two modes below.

In a heating mode, at least two heating circuits are provided. The at least two heating circuits are electrically connected to the control module 12 separately and are in one-to-one correspondence with the at least two atomization compartments 21. Each heating circuit is configured to heat a corresponding atomization compartment 21. That is, when a preset atomization compartment needs to be heated, the heating circuit corresponding to the atomization compartment is turned on and other heating circuits are turned off so that the preset atomization compartment is heated. In this case, the heating circuits are connected in parallel.

In another heating mode, one heating circuit is provided. Moreover, the atomization housing 22 is provided with a switching component electrically connected to the control assembly 12. The heating circuit is secured on the switching component. The control assembly 12 can control the switching component to move so that the switching component drives the heating circuit to move to any one of the atomization compartments 21 and thus heats the atomization compartment 21. In an embodiment, when a preset atomization compartment needs to be heated, the control assembly 12 firstly controls the switching component to act and drive the heating circuit to move to the preset atomization compartment. Then the control assembly 12 controls the heating circuit to turn on so that the heating circuit only heats the preset atomization compartment. Exemplarily, in this embodiment, the switching component may include a motor and a gear set.

In some embodiments, the heating circuit may also heat substances in two or more atomization compartments 21 simultaneously so that the substances in the two atomization compartments 21 are mixed to be inhaled by the user. Exemplarily, a plurality of heating circuits are provided. The control assembly 12 controls a plurality of heating circuits to turn on simultaneously and heat a plurality of atomization compartments 21 simultaneously. Alternatively, one heating circuit is provided. The control assembly controls the one heating circuit to heat a plurality of atomization compartments 21 simultaneously.

Figure 7:
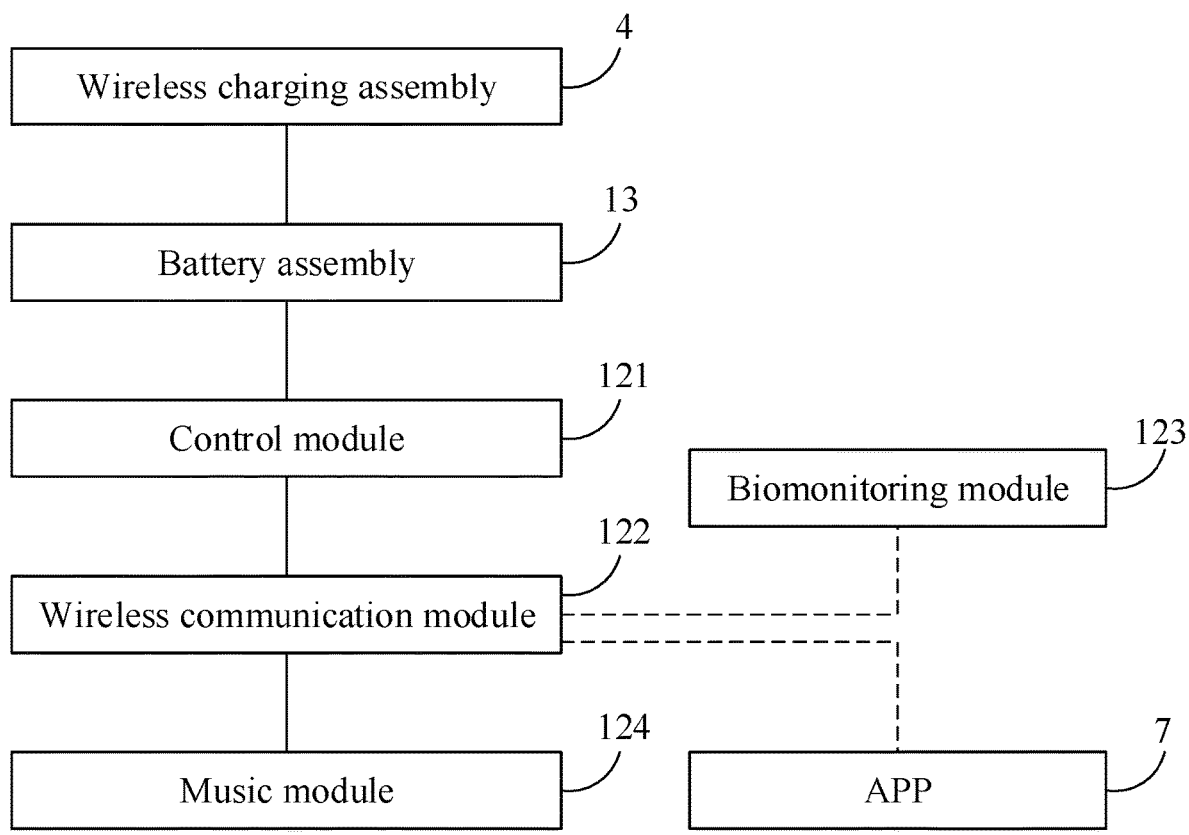
FIG. 7 is a diagram illustrating the connection of partial structures in an electronic atomization apparatus according to embodiments of the present disclosure.

As shown in FIG. 7, the control assembly 12 includes a control module 121 and a wireless communication module 122 electrically connected to the control module 121. The preceding heating circuit is electrically connected to the control module 121. The wireless communication module 122 is able to receive a wireless control signal and send the wireless control signal to the control module 121. The control module 121 is able to control the heating circuit to turn on or off according to the received wireless control signal. The wireless control signal may be sent by an APP 7 on an electronic terminal device. That is, the electronic atomization apparatus in this embodiment can perform wireless communication, for example, Bluetooth, infrared, and 5G, with an electronic terminal device. The user may input an instruction on the APP 7 on the electronic terminal device. The APP 7 generates a wireless control signal according to the instruction and sends the wireless control signal to the wireless communication module 122 so that the control module controls the heating circuit to, for example, turn on, turn off, increase power, or decrease power. Exemplarily, the wireless control signal includes the information of turning on, the information of turning off, the information of increasing temperature, and the information of decreasing temperature.

In an embodiment, the control module 121 may interact with the APP 7 on the electronic terminal device through the wireless communication module 122. For example, the control module 121 may transmit characteristic parameters of the electronic atomization apparatus to the APP 7 through the wireless communication module 122 so that the user can determine the operation state of the electronic atomization apparatus on the APP 7. The characteristic parameters include the temperature in each atomization compartment 21, the atomization compartment 21 being used, the remaining substance to be atomized in each atomization compartment 21, and the electric quantity of the battery assembly 13.

This helps the user know about the status of the electronic atomization apparatus more quickly.

Further, with continued reference to FIG. 7, the control assembly 12 further includes a biomonitoring module 123. The biomonitoring module 123 is electrically connected to the control module 121 and is configured to monitor the user-biometric information. Specifically, in the contact with the electronic atomization apparatus, the user may touch the electronic atomization apparatus. At this point, the biomonitoring module 123 can measure the heart rate. The mode of measuring the heart rate is similar to the mode of measuring the heart rate by a smart wearable device. Based on the absorption of light by substances, the pulse change of light transmittance in the blood is converted into an electric signal. In this case, whether the pulse moves normally and regularly is measurable. The biomonitoring module 123 may transmit the monitored user-biometric information to the control module 121. Then the control module 121 sends the user-biometric information through the wireless communication module 122 to the APP 7. In this case, the APP 7 makes statistics on the user-biometric information and thus feeds back the health condition of the human body. Exemplarily, the user-biometric information includes body temperature, heart rate, pulse, and the like.

In this embodiment, the battery assembly 13 provides electricity to structures including the biomonitoring module 123, the wireless communication module 122, and the heating circuit through the control module 121. Moreover, the battery assembly 13 in this embodiment includes a graphene battery with fast charging efficiency and stability.

Further, as shown in FIG. 4, the electronic atomization apparatus further includes a wireless charging assembly 4 electrically connected to the battery assembly 13. In this case, the wireless charging of the electronic atomization apparatus is implemented and the charging convenience is improved. It is to be understood that, as shown in FIG. 1, the electronic atomization apparatus further includes a USB-C data charging connector 6 electrically connected to the battery assembly 13. In this case, the battery assembly 13 can be charged through a data line and a charger. In this embodiment, the electronic atomization apparatus further has the function of an LED charging display. Exemplarily, the electronic atomization apparatus is provided with an LED display panel for displaying the charging process of the electronic atomization apparatus.

Figure 2:
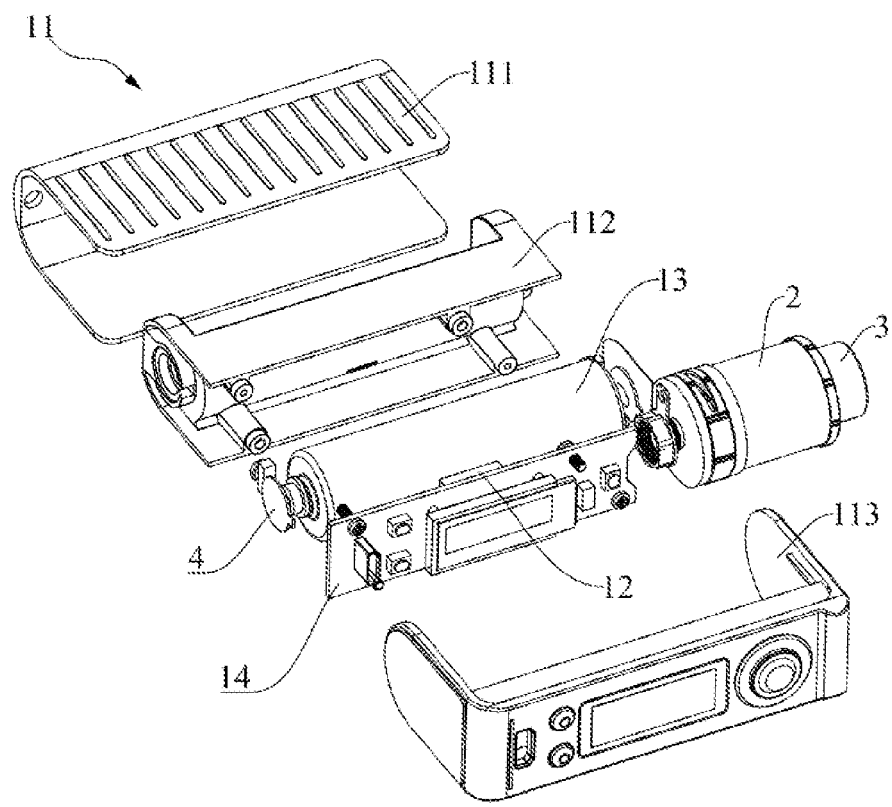
FIG. 2 is a view illustrating the decomposed structure of an electronic atomization apparatus according to embodiments of the present disclosure.
Figure 3:
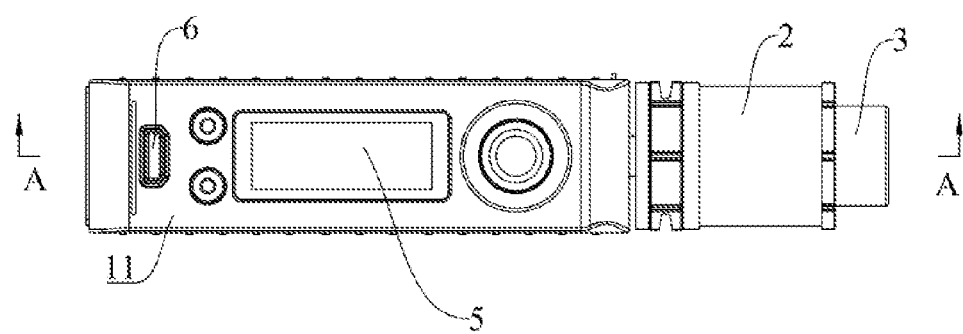
FIG. 3 is a top view of an electronic atomization apparatus according to embodiments of the present disclosure.

As shown in FIG. 2, the housing component 11 includes a housing (not shown) and a separator 112 secured inside the housing. One end of the atomization housing 11 of the atomizer 2 is connected to one end of the housing. The separator 112 separates the housing into a battery cavity and an electronic cavity. The preceding battery assembly 13 is secured inside the battery cavity. The control assembly 12 is secured inside the electronic cavity. The wireless charging assembly 4 is secured on the housing and disposed at the end of the battery assembly 13. Exemplarily, as shown in FIG. 2, the housing includes a first sub-housing 111 and a second sub-housing 113 that are connected to each other. The separator 112 and a part of the first sub-housing 111 form the battery cavity. The separator 112, another part of the first sub-housing 111, and the second sub-housing 113 form the electronic cavity.

In an embodiment, the electronic atomization apparatus further includes a touch display panel 5 disposed on the second sub-housing 113. The touch display panel 5 is an OLED display panel and is electrically connected to the control assembly 12. A control instruction may be input through the touch display panel 5 to the control module 121 to enable that the control module 12 controls the operation state of the atomizer 2 according to the control instruction. In the case where the touch display panel 5 can display a touch switch, the control assembly 12 turns on or off the atomizer 2 when the user touches the touch switch.

Further, as shown in FIG. 7, the control assembly 12 further includes a music module 124. The music module 124 is electrically connected to the battery assembly 13, the wireless communication module 122, and the control module 121. A music instruction may be input through the APP 7 or the touch display panel 5 to the control module 121 to enable that the control module initiates a music control signal to the music module 124 according to the music instruction. The music module 124 can play music according to the music control signal. Alternatively, the music module 124 transmits music through an external connection device so that the music is played through the external connection device.

In this embodiment, the electrical connection between the control module 121 and the wireless communication module 122, the electrical connection between the control module 121 and the biomonitoring module 123, and the electrical connection between the control module 121 and the heating circuit may be implemented through a circuit board 14. In an embodiment, the circuit board 14 is secured on the second sub-housing 113.

The preceding embodiments describe only the basic principles and characteristics of the present disclosure and the present disclosure is not limited to the preceding embodiments. Various modifications and changes may be made in the present disclosure without departing from the spirit and scope of the present disclosure. These modifications and changes fall within the scope of the present disclosure. The scope of the present disclosure is defined by the appended claims and equivalents thereof

What is claimed is:

1. An electronic atomization apparatus, comprising:
    a main unit comprising a housing component, a control assembly, and a battery assembly, wherein the control assembly and the battery assembly are disposed inside the housing component, and the control assembly is electrically connected to the battery assembly; and
    an atomizer comprising an atomization housing and a heating circuit disposed inside the atomization housing, wherein one end of the atomization housing is connected to one end of the housing component, the atomization housing is provided with at least two atomization compartments that are independent of each other, the heating circuit is electrically connected to the control assembly, another end of the atomization housing is provided with a gas outlet, and the gas outlet is selectively communicated with one atomization compartment of the at least two atomization compartments;
    wherein the electronic atomization apparatus comprises only one heating circuit, the atomization housing is provided with a switching component electrically connected to the control assembly, and the only one heating circuit is secured on the switching component;
    wherein the switching component is configured to drive the only one heating circuit to move to any one of the at least two atomization compartments.

2. The electronic atomization apparatus according to claim 1, wherein the one end of the atomization housing is detachably connected to the one end of the housing component.

3. The electronic atomization apparatus according to claim 1, further comprising a nozzle, wherein the nozzle is connected to the another end of the atomization housing and communicated with the gas outlet.

4. The electronic atomization apparatus according to claim 1, wherein the control assembly comprises a control module and a wireless communication module electrically connected to the control module, the heating circuit is electrically connected to the control module, the wireless communication module is able to receive a wireless control signal, the control module is able to control the heating circuit to turn on or off according to the wireless control signal, and the wireless control signal comprises information of turning on or information of turning off.

5. The electronic atomization apparatus according to claim 4, wherein the control assembly further comprises a biomonitoring module, the biomonitoring module is electrically connected to the control module and is configured to monitor user-biometric information, and the user-biometric information comprises body temperature or heart rate.

6. The electronic atomization apparatus according to claim 1, wherein the battery assembly comprises a graphene battery.

7. The electronic atomization apparatus according to claim 6, further comprising a wireless charging assembly electrically connected to the battery assembly.

8. The electronic atomization apparatus according to claim 7, wherein the housing component comprises a housing and a separator secured inside the housing, the one end of the atomization housing is connected to one end of the housing, the separator is configured to separate the housing into a battery cavity and an electronic cavity, the battery assembly is secured inside the battery cavity, the control assembly is secured inside the electronic cavity, and the wireless charging assembly is secured on the housing and disposed at one end of the battery assembly.

9. The electronic atomization apparatus according to claim 8, further comprising a touch display panel disposed on the housing, wherein the touch display panel is electrically connected to the control assembly.

* * * * *